United States Patent [19]
Hodgkinson et al.

[11] Patent Number: 5,148,550
[45] Date of Patent: Sep. 22, 1992

[54] PROTECTIVE FACE AND HEAD GEAR

[75] Inventors: Robert F. Hodgkinson, Lake Forest; Peter J. Hylak, Northbrook; Gary L. Berge, Crystal Lake, all of Ill.

[73] Assignee: Hodgkinson Associates, Inc., Lake Bluff, Ill.

[21] Appl. No.: 687,504

[22] Filed: Apr. 19, 1991

[51] Int. Cl.$^5$ .............................................. A63B 71/10
[52] U.S. Cl. ............................................... 2/424; 2/425; 2/9; 2/441
[58] Field of Search ............... 2/424, 9, 10, 425, 452, 2/410, 411, 414

[56] References Cited

U.S. PATENT DOCUMENTS

| | | | |
|---|---|---|---|
| 2,665,686 | 1/1954 | Wood et al. | 2/9 X |
| 2,761,144 | 9/1956 | Shipman | 2/9 |
| 3,805,294 | 4/1974 | Rose et al. | 2/10 |
| 3,897,597 | 8/1975 | Kasper | 2/9 |
| 4,587,677 | 5/1986 | Clement | 2/424 |
| 4,653,124 | 3/1987 | McNeal | 2/9 |
| 4,754,501 | 7/1988 | Yahn | 2/9 X |
| 5,010,598 | 4/1991 | Flynn et al. | 2/424 X |

Primary Examiner—Peter Nerbun

[57] ABSTRACT

A field mask for protecting the face and head is disclosed. The mask includes a top portion, side portions, and a face portion. The face portion of the mask is flared outwardly at its lower end so that the wearer may lower his head without the lower end of the mask's face portion making contact with his throat. The mask is formed to permit the wearer to wear eye glasses and includes filter vents and a removable transparent lens.

8 Claims, 2 Drawing Sheets

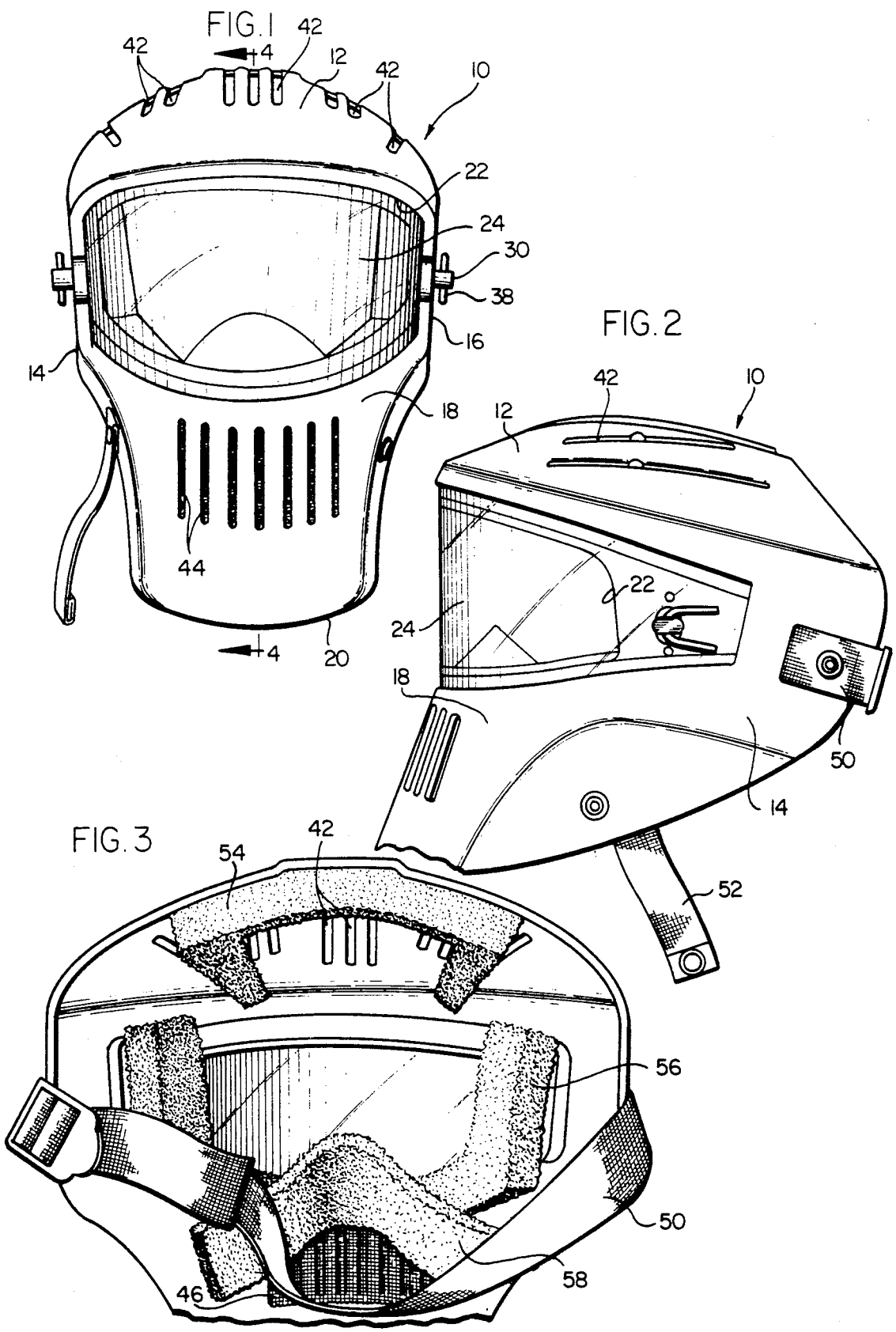

PROTECTIVE FACE AND HEAD GEAR

BACKGROUND OF THE INVENTION

This invention relates to protective face and head gear to be worn by an individual to protect his forehead, eyes, nose, mouth, ears and the top of his head from projectiles thrown or shot at the wearer. More particularly, it relates to protective face and head gear of the described type which is molded of a plastic material, is light-weight and inexpensive in comparison to helmet-type protective head gear, which primarily protects only the head and not the face. The protective face and head gear is hereinafter referred to as a field mask.

DESCRIPTION OF THE PRIOR ART

Protective head gear or helmets are worn for safety reasons by many individuals on their jobs and in playing many sports. In particular, most construction workers are required to wear "hard hats," one example of the many different types of protective head gear. In some instances workers wear both a hard hat and safety goggles to protect their heads and eyes from injury. In sports, football for example, the players wear football helmets to protect their heads. The same is true with hockey players. They generally wear face masks. These head gears and/or face masks therefore protect either the head or face, but not both. Furthermore, they do not protect both the face and head from objects thrown or shot at the wearer. Recently, another sport which has become popular is called "paint ball war games." During this game the players shoot paint pellets at one another. These paint pellets travel at a relatively high velocity, and if a player is hit in the face by one of them, serious injury can result. Helmets designed to protect the head from injury will not protect the face in such cases, and those designed to protect the face do not protect the head, particularly the ears and the back of the head.

SUMMARY OF THE INVENTION

The type of protective head gear used is as varied as the situations in which protective head gear is needed to be worn. The field mask of the present invention is extremely suitable for use by individuals playing "paint ball war games," as well as any type of job-related or sport-related activity wherein objects are thrown or shot at the wearer to protect both the face and head of the wearer, as will be apparent from the description below. The field mask is strong, light-weight, and relatively inexpensive in comparison to helmets which protect only the head and face masks which protect only the face. The field mask is molded of a plastic material such as virgin ABS or virgin nylon, depending on its specific use and the strength required. In some cases, it is preferred to use the virgin nylon because of its strength and its flexibility. For example, in playing the "paint ball war games," if the field mask is struck by a paint pellet traveling at a high velocity, it will absorb the impact and will not crack or shatter. The field mask is vented and includes die-cut foam liners or padding for cushioning the face and head for comfort. The field mask also has a transparent lens which provides a wide field of vision The lens is easily removed and replaced if desired. The lens also is provided in various colors. In addition, the field mask, unlike most existing helmets or face masks, is formed to permit eye glasses to be worn while wearing it. The field mask also includes a head strap which is adjustable and a chin strap which is of an elastic material so that the field mask can be comfortably secured against inadvertent loss during use. Accordingly, the field mask is adaptable for many different uses, whether it be job-related or sports-related.

OBJECT OF THE INVENTION

It is therefore an object of the invention to provide an improved light-weight, inexpensive protective face and head gear which is adaptable for many different uses, whether it be job related or sports related.

More particularly still, it is an object of the invention to provide an improved protective face and head gear which protects both the face and head of the user.

DESCRIPTION OF THE DRAWINGS

FIG. 1 is a front plan view of the field mask of the invention;

FIG. 2 is a side plan view of the field mask of FIG. 1;

FIG. 3 is a bottom plan view of the field mask of FIG. 1;

DETAILED DESCRIPTION OF THE INVENTION

Figure 4:
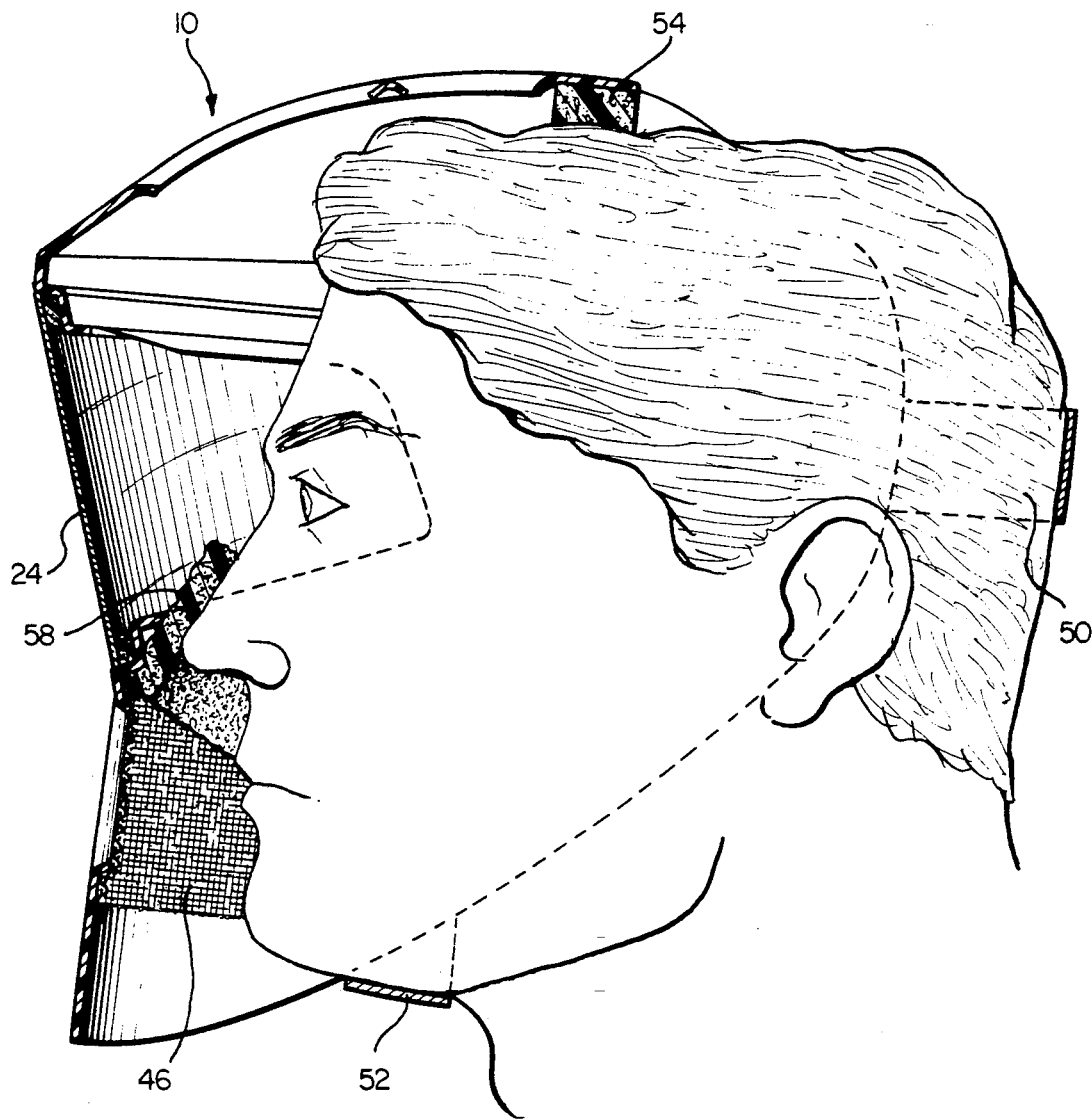
FIG. 4 is a sectional view taken along lines 4—4 of FIG. 1.

Referring now to the drawings, there is illustrated a field mask 10 exemplary of the invention having a top portion 12, side portions 14 and 16, and a front or face portion 18, all integrally molded of a plastic material. The top portion 12, side portions 14, 16 and face portion 18 are shaped so as to flow together to form a shell which extends across the top of the head and about the sides of the head. The face portion 18 covers the face and, more importantly, is formed to extend outwardly in front and the sides so that glasses can be easily and comfortably worn by the user. The face portion 18 also covers a portion of the throat and is flared outwardly at its lower end 20 so that the head can be easily pivoted down in front without the lower end 20 of the face portion 18 contacting the throat.

Figure 5:
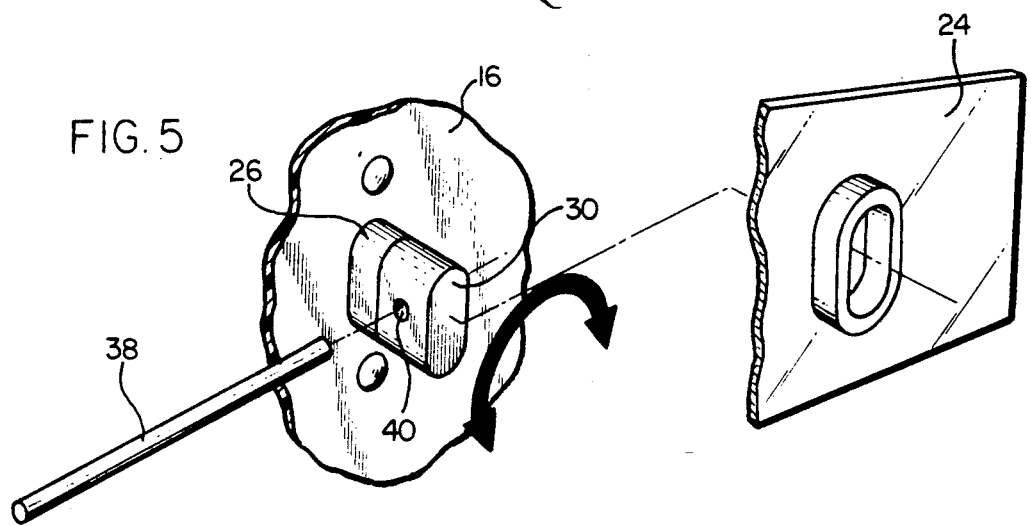
FIG. 5 is a partial plan view of the field mask illustrating the fastener means and the safety lock, and the manner in which they removably secured the lens to the field mask.

An opening 22 is formed in the face portion 18 and extends around the respective side portions 14 and 16 so as to provide an opening which gives the wearer a field of vision of approximately 180° through the face and side portions. The opening 22 is covered with a transparent lens 24 which is removably affixed to the head gear 10 by means of a pair of fastener means 26 and 28. The fastener means 26, 28 (FIG. 5), as illustrated, comprise a pair of studs affixed to the side portions 14, 16 and have ends 30 and 32 which are rotatable to lock and release the lens 24. The lens 24 has a pair of slots 34 and 36 formed in it for receiving therethrough the studs 26, 28, and once the studs are extended through the slots, the ends 30 and 32 are rotated to lock the lens in place. A safety lock 38 in the form of a wire is provided for each of the studs to prevent the lens from being inadvertently detached from the field mask 10. The wires 38 are extended through apertures 40 formed in the ends of the studs and prevent the lens from being detached if the ends of the studs are rotated to a position which would permit the studs to disengage from the slots in the lens through which the studs extend. Other types of fastener means and safety locks likewise can be used. The lens preferably is of a clear plastic composite which has chemical and impact resistance, such as polycarbonate, to resist shattering if it is struck by another object and to prevent paint or other materials from marring the transparency of the lens before or after cleaning the lens. The lens also can be provided in different colors.

The top portion 12 of the lens 10 also has a number of air vents 42 formed in it to provide air circulation through the field mask. These air vents can be in the form of elongated, spaced-apart slots, as illustrated, or another suitable shape to provide air flow into the field mask.

The face portion 18 also has air vents 44 formed in it across the lower edge 20 which flares outwardly, and these air vents 44 likewise are in the form of vertically extending, spaced-apart slots. These air vents 44 have a filter-type shield 46 (FIG. 3) affixed behind them on the inner side of the field mask in the form of a black screen for preventing dust and other forms of particulate matter from being inhaled through the air vents. The screen can be adhesively or otherwise affixed to the field mask. The air vents 42 and 44 not only provide ventilation but also resist fogging of the lens 24.

The field mask has two straps 50, 52 for securing it to an individual's head. One of these two straps is an adjustable two-piece strap 50 which is affixed to the field mask so as to extend around the back of the head. This strap 50 is adjustable to permit the wearer to tighten the strap as he may desire to secure the field mask on his head. The other of the two straps 52 functions as a chin strap and comprises an elastic band, the ends of which are affixed respectively to the opposite sides of the field mask so as to extend under the chin of the wearer.

The inside of the field mask has a number of die-cut foam liners or pads for the face and head. One of these pads 54 is generally U-shaped and is adhesively or otherwise affixed inside of the field mask to the top portion 12 to provide padding for the top of the head and so as to not block the air flow through the air vents 42 in the top portion 12 of the field mask. Another one of the pads 56 is adhesively or otherwise affixed to the inside of the face portion 18 of the field mask so as to provide padding for the face, particularly the cheeks. Still another one of the pads 58 is adhesively or otherwise affixed to the field mask so as to provide padding for the face and particularly the nose.

Accordingly, from the above description, it can be seen that a field mask which is strong, light-weight and relatively inexpensive is provided. The field mask is vented and has foam liners or padding for cushioning the head and face for comfort. The field mask permits a user to wear eye glasses and has a transparent lens which provides a wide field of vision. The lens also is easily and quickly replaceable. In addition, the field mask has a head strap and a chin strap so that it can be secured comfortably on the head.

What is claimed is:

1. A field mask to be worn on the head by an individual to protect both his face and head, including his forehead, eyes, nose, mouth, ears, throat and top of his head, particularly from objects thrown or shot at the wearer, comprising, in combination:
   a shell molded of a plastic material and having a top portion, side portions and a face portion all integrally formed and shaped to receive therein the head of an individual;
   said top portion covering the top of the wearer's head and having formed therein a plurality of first vents for providing air flow through said head gear;
   said side portions covering the sides of the wearer's head and extending below the wearer's ears;
   said face portion covering the wearer's face and extending to cover a portion of the wearer's throat, said face portion further being flared outwardly at its lower end so that the head can be easily pivoted down in front without the lower end of the face portion contacting the throat;
   a plurality of second vents formed in said face portion for providing air flow through said head gear;
   a shield affixed behind said second vents for preventing dust and the like from being inhaled through said second vents;
   said side portions and said face portion being formed to permit the wear to wear eye glasses while wearing said field mask and having formed therein an opening that extends across said face portion and each of said side portions so as to provide a wide field of vision through said face and side portions when looking out of said field mask through said opening; and
   a transparent lens removably secured over said opening.

2. The field mask of claim 1, wherein said lens has a pair of slots formed in it, fastening means affixed to each side portion of said field mask for removably securing said transparent lens over said opening, said fastening means extending through said slots in said lens and including safety locks for preventing said lens from being inadvertently removed from said field mask.

3. The field mask of claim 2 being molded of a virgin ABS plastic material.

4. The field mask of claim 2 being molded of a virgin nylon plastic material.

5. The field mask of claim 2 wherein said transparent lens is of a plastic composite which has chemical and impact resistance.

6. The field mask of claim 5 wherein said transparent lens is of a polycarbonate material.

7. The field mask of claim 2 further comprising a first strap affixed to said side portions and extendable about the back of an individual's head, said first strap being adjustable to securely fit said head gear to the individual's head;
   a second strap affixed to said side portions and extendable about the chin of an individual, said second strap being of an elastic material; and
   a plurality of liners disposed within said head gear for cushioning said head gear on an individual's head.

8. The field mask of claim, 7 wherein said plurality of liners comprises die-cut foam liners, said liners being adhesively affixed within said shell to protect the individual's head and face.

* * * * *